United States Patent [19]

Kaplan

[11] 4,151,192

[45] Apr. 24, 1979

[54] PROMOTING N-PROPYL ALCOHOL FORMATION WITH VANADIUM COMPOUNDS

[75] Inventor: Leonard Kaplan, Charleston, W. Va.

[73] Assignee: Union Carbide Corporation, New York, N.Y.

[21] Appl. No.: 906,585

[22] Filed: May 16, 1978

[51] Int. Cl.$^2$ ...................... C07C 27/06; C07C 31/02; C07C 31/20
[52] U.S. Cl. .............................. 260/449 L; 260/449.5
[58] Field of Search ............. 260/449 L, 449 R, 449.5

[56] References Cited

U.S. PATENT DOCUMENTS 3,833,634  9/1974  Pruett et al. ..................... 260/449 R Primary Examiner—Howard T. Mars
Attorney, Agent, or Firm—Donald M. Papuga

[57] ABSTRACT

This invention relates to the manufacture of monohydric and polyhydric alcohols, specifically, n-propyl alcohol by reacting synthesis gas, i.e., hydrogen and oxides of carbon, in the presence of a rhodium carbonyl complex and vanadium compounds.

13 Claims, No Drawings

PROMOTING N-PROPYL ALCOHOL FORMATION WITH VANADIUM COMPOUNDS

This invention relates to the production of monohydric and polyhydric alcohols.

Specifically, this invention is directed to the process of making monohydric alcohols, particularly, n-propyl alcohol, alkane diols and triols, containing 1,2,3 or 4 carbon atoms. Key products of the process of this invention are n-propyl alcohol and ethylene glycol. By-products of this invention are the lesser valuable, but valuable nevertheless, monohydric alkanols such as methanol. The products of the process of this invention contain carbon, hydrogen and oxygen.

There are described in U.S. Pat. No. 3,833,634 issued Sept. 3, 1974, and U.S. Pat. No. 3,957,857, issued May 18, 1976, processes for reacting hydrogen and oxides of carbon in the presence of rhodium carbonyl complex catalysts to produce polyhydric alcohols, such as ethylene glycol and monohydric alcohols, such as methanol.

The conditions employed in those processes involve reacting a mixture of an oxide of carbon and hydrogen with a catalytic amount of rhodium in complex combination with carbon monoxide, at a temperature of between about 100° C. and about 375° C. and a pressure of between about 500 psia and about 50,000 psia.

In addition to the aforementioned U.S. Patents, the following U.S. Patents and U.S. Patent Applications amplify the development of the processes for making alkane monohydric and polyhydric alcohols from mixtures of hydrogen and oxides of carbon:

| | |
|---|---|
| U.S. Pat. 3,878,292 | Patented April 15, 1975 |
| U.S. Pat. 3,878,290 | Patented April 15, 1975 |
| U.S. Pat. 3,878,214 | Patented April 15, 1975 |
| U.S. Pat. 3,886,364 | Patented May 27, 1975 |
| U.S. Pat. 3,940,432 | Patented February 24, 1976 |
| U.S. Pat. 3,929,969 | Patented December 30, 1975 |
| U.S. Pat. 3,952,039 | Patented April 20, 1976 |
| U.S. Pat. 3,948,965 | Patented April 6, 1976 |
| U.S. Pat. 3,944,588 | Patented March 16, 1976 |
| U.S. Pat. 3,957,857 | Patented May 18, 1976 |
| U.S. Ser. No. 455,380 | Filed March 27, 1974 |
| U.S. Ser. No. 455,379 | Filed March 27, 1974 |
| U.S. Ser. No. 526,942 | Filed November 25, 1974 |
| U.S. Ser. No. 488,139 | Filed July 12, 1974 |
| U.S. Ser. No. 488,140 | Filed July 12, 1974 |
| U.S. Ser. No. 506,862 | Filed September 17, 1974 |
| U.S. Ser. No. 506,864 | Filed September 17, 1974 |
| U.S. Ser. No. 506,865 | Filed September 17, 1974 |
| U.S. Ser. No. 511,740 | Filed October 3, 1974 |
| U.S. Ser. No. 615,093 | Filed September 19, 1975 |
| U.S. Ser. No. 537,885 | Filed January 2, 1975 |
| U.S. Ser. No. 618,023 | Filed September 30, 1975 |
| U.S. Ser. No. 618,061 | Filed September 30, 1975 |
| U.S. Ser. No. 618,021 | Filed September 30, 1975 |
| U.S. Ser. No. 727,646 | Filed September 29, 1976 |
| U.S. Ser. No. 782,986 | Filed March 30, 1977 |

It has been found that n-propyl alcohol can be produced from synthesis gas in a homogeneous liquid reaction mixture containing a catalytic amount of rhodium carbonyl complex and vanadium compounds.

This invention is thus directed to a process for producing alkane monohydric and polyhydric alcohols in a homogeneous liquid phase mixture which comprises reacting hydrogen and oxides of carbon in the presence of a rhodium carbonyl complex and compounds of vanadium at a temperature between about 100° C. and about 375° C. correlated with a pressure between about 500 psia and about 50,000 psia sufficient to produce said alcohols.

The compounds of vanadium suitable for use in this invention include vanadate esters, vanadium alkanedionates, alkanolamine vanadates, vanadium oxides, vanadium carbonyls, vanadyl carboxylates and salts containing vanadium oxyanions, etc.

The compounds of vanadium are desirably added with the initial charge of reactants in amounts of about 0.2 to about 30 millimoles, preferably, from about 1 to about 10 millimoles per millimole of rhodium.

The rhodium carbonyl complex catalysts suitable for use herein may be in the form of rhodium carbonyl clusters. P. Chini, in a review article entitled "The Closed Metal Carbonyl Clusters" published in Review (1968), Inorganica Chimica Acta, pages 30–50, states that a metal cluster compound is "a finite group of metal atoms which are held together entirely, mainly, or at least to a significant extent by bonds directly between the metal atoms even though some non metal atoms may be associated intimately with the cluster." The rhodium carbonyl clusters contain rhodium bonded to rhodium or rhodium bonded to another metal, such as cobalt and/or iridium. The preferred rhodium carbonyl cluster compounds are those which contain rhodium-rhodium bonds. These compounds desirably contain carbon and oxygen in the form of carbonyl (—CO), in which the carbonyl may be "terminal", "edge-bridging", and/or "face-bridging." They may also contain hydrogen and carbon in forms other than carbonyl.

Illustrative structures of two distinct rhodium carbonyl clusters, $Rh_6(CO)_{16}$ and $[Rh_{12}(CO)_{30}]^{2-}$ are disclosed in U.S. Pat. No. 3,957,857.

The structures of the rhodium carbonyl clusters may be ascertained by X-ray crystal diffraction, nuclear magnetic resonance (NMR) spectra, or infrared spectra as disclosed in the article entitled "Synthesis and Properties of the Derivatives of the $[Rh_{12}(CO)_{30}]^{-2}$ Anion" by P. Chini and S. Martinengo; appearing in Inorganica Chimica Acta, 3:2 pp 299–302, June (1969).

A number of nitrogen and/or oxygen-containing bases may be used in the process of the present invention. For the purposes of this invention, the bases can be considered to promote the activity of the rhodium catalysts. Nitrogen Lewis bases used as promoters generally contain hydrogen and nitrogen atoms. They may also contain carbon and/or oxygen atoms. They may be organic or inorganic compounds. With respect to the organic compounds, the carbon atoms can be part of an acyclic and/or cyclic radical such as aliphatic, cycloaliphatic, aromatic (including fused and bridged) carbon radicals, and the like. Preferably, the organic Lewis bases contain from 2 to 60, most preferably 2 to 40 carbon atoms. The nitrogen atoms can be in the form of imino (—N=) amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic), carboxyl

carbonyloxy oxy (—O—), carbonyl 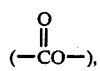

etc., all of said groups containing Lewis base oxygen atoms. In this respect, it is the "hydroxyl" oxygen in the

group and the "oxy" oxygen in the

group that are acting as Lewis base atoms. The organic Lewis bases may also contain other atoms and/or groups as substituents of the aforementioned radicals, such as alkyl, cycloalkyl, aryl, chloro, trialkylsilyl substituents.

Illustrative of organic aza-oxa Lewis bases are, for example, the alkanolamines, such as, ethanolamine, diethanolamine, isopropanolamine, di-n-propanolamine, and the like; N,N-dimethylglycine, N,N-diethylglycine; iminodiacetic acid, N-methyliminodiacetic acid; N-methyldiethanolamine; 2-hydroxypyridine, 2,4-dihydroxypyridine, 2-methoxypyridine, 2,6-dimethoxypyridine, 2-ethoxypyridine; lower alkyl substituted hydroxypyridines, such as 4-methyl-2-hydroxypyridine, 4-methyl-2,6-dihydroxypyridine, and the like; morpholine, substituted morpholines, such as 4-methylmorpholine, 4-phenylmorpholine; picolinic acid, methyl-substituted picolinic acid; nitrilotriacetic acid, 2,5-dicarboxypiperazine, N-(2-hydroxyethyl) imino-diacetic acid, ethylenediaminetetraacetic acid; 2,6-dicarboxypyridine; 8-hydroxyquinoline, 2-carboxyquinoline, cyclohexane-1,2-diamine-N,N,N',N'-tetraacetic acid, the tetramethyl ester of ethylenediamine-tetraacetic acid, and the like.

Other Lewis base nitrogen containing compounds include organic and inorganic amines.

Illustrative of such inorganic amines are, e.g., ammonia, hydroxylamine, and hydrazine. Primary, secondary, or tertiary organic amines are promoters. This includes the mono- and polyamines (such as di-, tri-, tetraamines, etc.) and those compounds in which the Lewis base nitrogen forms part of a ring structure as in pyridine, quinoline, pyrimidine, hexamethylenetetraamine, and the like. In addition any compounds capable of yielding an amino nitrogen under the reaction conditions of the present invention are promoters, as in the case of an amide, such as formamide, cyanamide, and urea, or an oxime. Further illustrative of Lewis base nitrogen compounds are aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; aliphatic and aromatic di- and polyamines such as 1,2-ethanediamine, 1,3-propanediamine, N,N,N',N'-tetramethylenediamine, N,N,N',N'-tetraethylethylenediamine, N,N,N',N'-tetra-n-propylethylenediamine, N,N,N',N'-tetrabutylethylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like; aromatic amines such as aniline, 1-naphthylamine, 2-naphthylamine, p-toluidine, o-3-xylidine, p-2-xylidine, benzylamine, diphenylamine, dimethylaniline, diethylaniline, N-phenyl-1-naphthylamine, bis(1,8)-dimethylaminonaphthalene, and the like; alicyclic amines such as cyclohexylamine, dicyclohexylamine, and the like; heterocyclic amines such as piperidine; substituted piperidines such as 2-methylpiperidine, 4-ethylpiperidine, and 3-phenylpiperidine; pyridine; substituted pyridines such as 2-methylpyridine, 2-phenylpyridine, 2-methyl-4-ethylpyridine, 2,4,6-trimethylpyridine, 2-dodecylpyridine, 2-chloropyridine, and 2-(dimethylamino) pyridine; quinoline; substituted quinolines, such as 2-(dimethylamino)-6-methoxyquinoline; 4,5-phenanthroline; 1,8-phenanthroline; 1,5-phenanthroline; piperazine; substituted piperazines such as N-methylpiperazine, N-ethylpiperazine, 2-methyl-N-methylpiperazine; 2,2'-dipyridyl, methyl-substituted 2,2'-dipyridyl; ethyl-substituted 2,2'-dipyridyl; 4-triethylsilyl-2,2'-dipyridyl; 1,4-diazabicyclo[2.2.2.] octane, methyl substituted 1,4-diazabicyclo[2.2.2] octane, purine and the like.

Also included herein are the use of dimorpholine compounds characterized by the formula:

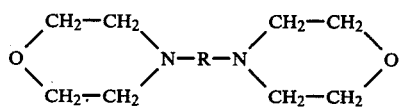

wherein R is alkylene of 1 to about 30 carbon atoms and 1,4-phenylene.

The base provided to the reaction mixture is present in an amount which is equal to or greater than that amount, determined from its basicity, which achieves the optimum rate of formation of said alkane polyol at said correlated catalyst concentration, temperature and pressure of such reaction mixture.

The concentration of the base will typically be within about 0.001 to about 10 molar. Obviously this range is definitive of the potential scatter of concentrations predicated on the varieties of the basicity of the base available.

Under reaction conditions the base is preferably used in amounts from about 0.02 to about 40 equivalents of base, most preferably from about 0.1 to about 20 equivalents base, for every atom of rhodium in the reaction mixture. The number of equivalents of base is equal to the number of molecules of base times the number of nitrogen atoms in each molecule.

In practicing the method of the present invention, the synthesis of n-propyl alcohol and alkane monohydric and polyhydric alcohols by the reaction of hydrogen with an oxide of carbon, is suitably conducted under operative conditions, as heretofore described, which give reasonable reaction rates and/or conversions.

The process is suitably effected over a wide superatmospheric pressure range between about 800 psia and about 50,000 psia. Pressures as high as 50,000 psia, and higher can be employed but with no apparent advantages attendant thereto which offset the unattractive plant investment outlay required for such high pressure equipment. Therefore, the upper pressure limitation is desirably approximately 16,000 psia. Effecting the present process below about 16,000 psia, especially below about 13,000 psia, and preferably at pressures below about 8,000 psia, results in cost advantages which are associated with low pressure equipment requirements. In attempting to foresee a commercial operation of this process, pressures between about 4,000 psia and 16,000 psia appear to represent most realistic values.

In a preferred embodiment of the present invention the pressures referred to above represent the total pressures of hydrogen and oxides of carbon in the reactor.

The process of this invention can also be carried out by providing salts in the homogeneous liquid phase reaction mixture. Suitable salts include any organic or inorganic salt which does not adversely affect the production of polyhydric alcohols. Experimental work suggest that any salt is beneficial as either a promoter, copromoter and/or in aiding in maintaining rhodium in solution during the reaction. Illustrative of the salts useful in the practice of the present invention are the ammonium salts and the salts of the metals of Group I and Group II of the Periodic Table (Handbook of Chemistry and Physics - 50th Edition) for instance the halide, hydroxide, alkoxide, phenoxide and carboxylate salts such as sodium fluoride, cesium fluoride, cesium pyridinolate, cesium formate, cesium acetate, cesium benzoate, cesium p-methylsulfonylbenzoate ($CH_3SO_2C_6H_4COO$)Cs, rubidium acetate, magnesium acetate, strontinum acetate, ammonium formate, ammonium benzoate and the like. Preferred are the cesium, rubidium, potassium, and ammonium salts.

Also useful in the practice of the present invention are organic salts of the following formula:

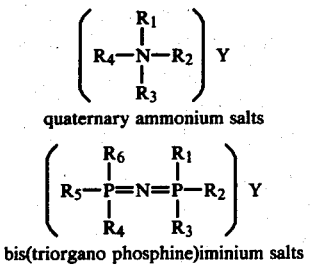

quaternary ammonium salts    I bis(triorgano phosphine)iminium salts    II wherein $R_1$ through $R_6$ in formulas (II) and (III) above are any organic radicals which do not adversely affect the production of polyhydric alcohols by reacting oxides of carbon with hydrogen in the presence of the aforedefined rhodium carbonyl complex, such as a straight or branched chain alkyl group, having from 1 to 20 carbon atoms in the alkyl chain, such as methyl, ethyl, n-propyl, isopropyl, n-butyl, octyl, 2-ethylhexyl, dodecyl, and the like; or a cycloaliphatic group including the monocyclic and bicyclic groups cyclopentyl, and bicyclo[2.2.1] heptyl groups, and the like or an aryl, alkylaryl, or aralkyl group such as phenyl, naphthyl, xylyl, tolyl, t-butylphenyl, benzyl, beta-phenylethyl, 3-phenylpropyl and the like; or a functionally substituted alkyl such as beta-hydroxyethyl, ethoxymethyl, ethoxyethyl, phenoxyethyl, and the like; or a polyalkylene ether group of the formula $(C_nH_{2n}O)x$-OR wherein n has an average value from 1 to 4, x has an average value from 2 to about 150, and R may be hydrogen or alkyl of 1 to about 12 carbon atoms. Illustrative of such polyalkylene ether groups are poly(oxyethylene), poly(oxypropylene), poly(oxyethyleneoxypropylene), poly(oxyethyleneoxybutylene), and the like. Y in formulas I and II above may be any anion which does not adversely affect the production of polyhydric alcohols in the practice of the present invention such as hydroxide; a halide, for instance fluoride, chloride, bromide and iodide; a carboxylate group, such as formate, acetate, propionate, and benzoate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pyridinolate or quinolate group; and others. Preferably Y in formulas I and II, above, is a carboxylate.

A suitable method for preparing the bis (triorganophosphine) iminium salts is disclosed in an article by Appel, R. and Hanas, A. appearing in Z. Anorg. u. Allg. Chem., 311, 290 (1961).

Other organic salts useful in the practice of the present invention include the quaternized heterocyclic amine salts such as the pyridinium, piperidinium, morpholinium, quinolinium salts and the like, e.g., N-ethylpyridinium fluoride, N-methylmorpholinium benzoate, N-phenylpiperidinium hydroxide, N,N'-dimethyl-2,2-bipyridinium acetate, and the like.

In addition, the anion of the above salt may be any of the rhodium carbonyl anions. Suitable rhodium carbonyl anions include $[Rh_6(CO)_{15}]^{2-}$; $[Rh_6(CO)_{15}Y]^-$ wherein Y may be halogen, such as chlorine, bromine, or iodine, $[Rh_6(CO)_{15}(COOR'')]^-$ wherein R'' is lower alkyl or aryl such as methyl, ethyl, or phenyl; $[Rh_6(CO)_{14}]^{2-}$; $[Rh_7(CO)_{16}]^{3-}$; $[Rh_{12}(CO)_{30}]^{2-}$; $Rh_{13}(CO)_{24}H_3^{-2}$; and $Rh_{13}(CO)_{24}H_2^{-3}$.

Under reaction conditions where a salt is employed, the salt is desirably added with the initial charge of reactants in amounts of from about 0.5 to about 2.0 moles, preferably from about 0.8 to about 1.6 moles, and most preferably from about 0.9 to 1.4 moles of salt for every five atoms of rhodium present in the reaction mixture.

Illustrative solvents which are generally suitable in making the homogeneous mixture include, for example, ethers such as tetrahydrofuran, tetrahydropyran, diethyl ether, 1,2-dimethoxybenzene, 1,2-diethoxybenzene, the mono- and dialkyl ethers of ethylene glycol, of propylene glycol, of butylene glycol, of diethylene glycol, of butylene glycol, of diethylene glycol, of dipropylene glycol, of triethylene glycol, of tetraethylene glycol, of dibutylene glycol, of oxyethylenepropylene glycol, etc; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate etc.; water; gamma-butyrolactone, deltavalerolactone; substituted and unsubstituted tetrahydrothiophene-1,1-dioxides (sulfolanes) as disclosed in U.S. application Ser. No. 537,885, filed on Jan. 2, 1975, the disclosure at pages 6 and 7 of the specification of which is incorporated herein by reference.

Also, the crown ethers are suitable herein, particularly those as described in U.S. patent application Ser. No. 832,384 filed Sept. 13, 1977, which application is incorporated herein by reference. The crown ethers described therein contain at least four oxygen heteroatoms and include [18]-crown-6 and [15]-crown-5.

The preferred solvents for practising the invention are a number of solvents which have heretofore been described in the production of alkane polyols from synthesis gas.

Particularly desirable solvents are tetraglyme, sulfolane, gamma-butyrolactone and the crown ethers. Other very desirable solvents include mixtures of tetraglyme and sulfolane, mixtures of sulfolane and butyrolactone, mixtures of crown ethers and sulfolane, mixtures of crown ethers and tetraglyme, mixtures of crown ethers and butyrolactone, mixtures of tetraglyme and butyrolactone.

The temperature which may be employed can vary over a wide range of elevated temperatures. In general, the process can be conducted at a temperature in the range between about 100° C. and upwards to approximately 375° C., and higher. Temperatures outside this stated range are not excluded from the scope of the invention. At the lower end of the temperature range, and lower, the rate of reaction to desired product becomes markedly slow. At the upper temperature range, and beyond, signs of some catalyst instability are noted. Notwithstanding this factor, reaction continues and alkane monohydric and polyhydric alcohols and/or their derivatives are produced. Suitable temperatures are between about 150° C. and about 350° C., and desirably between about 210° C. and about 320° C.

The process is effected for a period of time sufficient to produce the alcohols.

In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressures exerted by its components, the concentration and choice of diluent, and other factors. The synthesis of the desired product(s) by the reaction of hydrogen with an oxide of carbon is suitably conducted under operative conditions which give reasonable reaction rates and/or conversions.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5.

It is understood, however, that molar ratios outside the aforesaid broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, monohydric and polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction.

Means to introduce and/or adjust the reactants, either intermittently or continuously, into the reaction zone during the course of the reaction can be conveniently utilized in the novel process especially to maintain the desired molar ratios of and the partial pressures exerted by the reactants.

The operative conditions can be adjusted to optimize the conversion of the desired product and/or the economics of the process. In a continuous process, for instance, when it is preferred to operate at relatively low conversions, it is generally desirable to recirculate unreacted synthesis gas with/without make-up carbon monoxide and hydrogen to the reaction. Recovery of the desired product can be achieved by methods well-known in the art such as by distillation, fractionation, extraction, and the like. A fraction comprising rhodium catalyst, generally contained in byproducts and/or normally liquid organic diluent, can be recycled to the reaction zone, if desired. All or a portion of such fraction can be removed for recovery of the rhodium values or regeneration to the active catalyst and intermittently added to the recycle stream or directly to the reaction zone.

The active forms of the rhodium carbonyl clusters may be prepared by various techniques. They can be preformed and then introduced into the reaction zone or they can be formed in situ.

The reaction of the present invention is conducted in what is believed to be a homogeneous liquid phase, which means that the catalyst, the vanadium compound promoter, the reaction products and other promoters which may be present are in solution. Though the reaction to produce alcohols is essentially homogeneous, there may be small amounts of insoluble catalyst particles depending on the reaction conditions employed.

The equipment arrangement and procedure which provides the capability for determining the existence of anionic rhodium carbonyl complexes or clusters having defined infrared spectrum characteristics, during the course of the manufacture of alcohols from carbon monoxide and hydrogen, pursuant to this invention is disclosed and schematically depicted in U.S. Pat. No. 3,957,857, the disclosure of which is incorporated herein by reference.

A particularly desirable infrared cell construction is described in U.S. Pat. No. 3,886,364, issued May 27, 1975, and its disclosure of a preferred cell construction is incorporated herein by reference.

The "oxide of carbon" as covered by the claims and as used herein is intended to mean carbon monoxide and mixtures of carbon dioxide and carbon monoxide, either introduced as such or formed in the reaction.

The following examples are merely illustrative and are not presented as a definition of the limits of the invention:

EXAMPLES 1 TO 21

A 150 ml. capacity stainless steel reactor capable of withstanding pressures up to 7,000 atmospheres was charged with a premix of 75 cubic centimeters (cc) of sulfolane solvent, 3.0 millimoles (mmol), 0.77 grams, of rhodium dicarbonylacetylacetonate, promoter(s) and one or more compounds of vanadium. The reactor was sealed and charged with a gaseous mixture, containing equal molar amounts of carbon monoxide and hydrogen to a pressure of 8,000 pounds per square inch (psig). Heat was applied to the reactor and its contents; when the temperature of the mixture inside the reaction reached 220° C., as measured by a suitably placed thermocouple, an additional adjustment of carbon monoxide and hydrogen ($H_2:CO=1:1$ mole ratio) was made to bring the pressure back to 8000 psig. The temperature (in ° C.) was maintained at the desired value for 4 hours. During this period of time additional carbon monoxide and hydrogen was added whenever the pressure inside the reactor dropped below about 7500 psig. With these added repressurizations the pressure inside the reactor was maintained at 8000 psig ± 400 over the entire 4 hour period.

After the 4 period, the vessel and its contents were cooled to room temperature, the excess gas vented and the reaction product mixture was removed. Analysis of the reaction product mixture was made by gas chromatographic analysis using a Hewlett Packard FM ™ model 810 Research Chromatograph.

The product weight (in grams) of n-propyl alcohol, methanol, ethylene glycol, "n-butyl alcohol", propylene glycol and glycerine, as determined from the analysis of the product mixture, are as listed in Table I.

Rhodium recovery was determined by atomic absorption analysis of the contents of the reactor after the venting of the unreacted gases at the end of the reaction. A further analysis was run on a "wash" of the reactor. The wash of the reactor consisted of charging to the reactor 100 cc of the solvent used for that experiment, and bringing the reactor and its contents to a temperature of 160° C. and a pressure of 14,000 to 15,000 psig and maintaining these conditions for a period of 30 minutes. The reactor was then cooled and the unreacted gases vented and an atomic absorption analysis for rhodium was run on the reactor's contents. The rhodium recovery values recited below are the percent rhodium based on the total rhodium charged to the reactor that is soluble or suspended in the reaction mixture plus the wash after the specified reaction time. The results are set forth in Table I.

The materials used in the following examples had the following characteristics:

Cesium formate (Alfa), ammonium benzoate (PCR "veripur" grade), tetraglyme (Ansul), tributyl vanadate (ROC/RIC), cesium meta-vanadate ($CsVO_3$), (ROC/RIC), vanadyl acetate [$VO(OAc)_3$] (ROC/RIC), triethylvanadate (Alfa), vanadium pentoxide (Alfa), cyclopentadienyl vanadium tetracarbonyl (Strem) and vanadium acetylacetonate (ROC/RIC), were used without further purification.

Sulfolane (Phillips) was purified as described by Arnett.[1] Cesium benzoate[2] (recryst. $H_2O$), Anal. Found: C,32.62: H, 1.90. Calcd. for $C_7H_5O_2Cs$: C, 33.10; H, 1.98), and triethanolamine vanadate[3] [mp (BuOH) 253°-7° (d); nmr (DMSO-$d_6$): $\tau=5.43$ (t, $J\approx5.5$ cps, 6.OH), 6.91 (t, $J\approx5.5$ cps, 6.OH)] were prepared by use of literature procedures.

References

[1] E. N. Arnett and C. F. Douty, J. Am. Chem. Soc., 86, 409 (1964).
[2] J. H. S. Green, W. Kynaston, and A. S. Lindsey, Spectrochim. Acta, 17, 486 (1961).
[3] M. G. Voronkov and A. Lapsina, Khim. Geterotsikl. Soedin., Akad. Nauk Latv. SSR, 357 (1966).

TABLE I
COMPOUNDS OF VANADIUM AS PROMOTERS OF n-PROPYL ALCOHOL FORMATION

| Examples | Salt (mmoles) | Amine (mmoles) | T° C. | V Compound (mmoles) | n-Propyl Alcohol, g | Methanol, g | Ethylene Glycol, g | n-butyl[e] Alcohol, g | Propylene Glycol, g | Glycerine, g | % Rh Recovered |
|---|---|---|---|---|---|---|---|---|---|---|---|
| 1 | HCO$_2$Cs(0.65) | — | 240 | — | — | 2.84 | 4.90 | — | — | — | 80 + 4 |
| 2 | " | — | " | Triethanolamine vanadate (2.5) | 0.27 | 3.40 | 1.32 | — | 0.28 | — | 83 + 6 |
| 3 | — | N-methylmorpholine (5.0) | " | — | — | 3.63 | 5.28 | — | — | — | 80 + 4 |
| 4 | — | " | " | — | — | 3.84 | 5.20 | — | — | — | 83 + 6 |
| 5 | — | " | " | — | — | 4.09 | 5.50 | — | — | — | 84 + 6 |
| 6 | — | " | " | — | — | 3.35 | 5.00 | — | — | — | 84 + 5 |
| 7 | — | " | " | — | — | 4.20 | 5.45 | — | — | — | 82 + 5 |
| 8 | — | " | " | — | — | 4.30 | 5.85 | — | — | — | 81 + 4 |
| 9 | — | " | " | Tributyl vanadate (3.05) | 0.54 | 4.58 | 0.80 | 0.61 | — | — | 78 + 5 |
| 10 | — | " | " | V(acetylacetonyl)$_3$ (2.93) | 0.27 | 4.26 | 1.71 | — | 0.62 | — | 77 + 6 |
| 11 | See V Compound Column | — | " | CsVO$_3$(0.65) | 0.05 | 2.52 | 0.59 | — | 0.05 | — | 93 |
| 12 | PhCO$_2$NH$_4$(0.65) | — | 260° | — | — | 4.53 | 4.90 | — | — | — | 66 + 3 |
| 13 | " | — | " | — | 1.00 | 4.90 | 1.10 | 0.18 | 0.16 | — | 82 + 8 |
| 14 | " | — | " | Triethanolamine vanadate (2.5) | 0.91 | 4.70 | 1.43 | 0.18 | 0.29 | — | 79 + 11 |
| 15 | " | — | " | Triethanolamine vanadate (2.5) + 6.0g ethylene glycol[b] | 1.70 | 5.08 | 3.70 | 0.18 | 0.68 | — | 68 + 4 |
| 16 | " | — | " | Triethanolamine vanadate (2.5) + 8.9g glycerine[c] | 0.93 | 5.44 | 2.74 | — | 1.22 | 3.44 | 80 + 4 |
| 17 | " | — | " | Triethanolamine vanadate (2.5) + 6.7g propylene glycol[d] | 0.82 | 5.15 | 1.70 | 1.13 | 1.65 | — | 71 + 7 |
| 18 | " | — | " | Vanadium Pentoxide (1.5) | 0.21 | 3.99 | 4.57 | 0.15 | 0.25 | — | 61 |
| 19 | " | — | " | Cyclopentadienyl vanadium tetracarbonyl (3) | 0.64 | 3.63 | 0.82 | 0.38 | 0.33 | — | 67 |
| 20 | " | — | " | Triethyl vanadate (3) | 0.68 | 4.15 | 1.26 | 0.35 | 0.50 | — | 72 |
| 21 | " | — | " | Vanadyl acetate (3) | 0.40 | 3.72 | 3.72 | 0.26 | 0.48 | — | 76 |

Data for all runs at H$_2$/CO = 1,8000 psig, 4 hr., 75 ml sulfolane, 3.0 mmoles rhodium
[b]Would analyze to be 5.4 g in the ethylene glycol column
[c]Would analyze to be 8.0 g in the glycerine column
[d]Would analyze to be 6.0 g in the propylene glycol column
[e]Identification tentative; based on vpc retention time

EXAMPLES 22 TO 28

The procedure of Examples 1 to 21 was exactly repeated except that the reaction was carried out in 75 ml. of tetraglyme solvent in the presence of salt, amine, vanadium compound and at the temperature as set forth in Table II below.

The product weight (in grams) of n-propyl alcohol, methanol, ethylene glycol, "n-butyl alcohol", propylene glycol and glycerine, as well as percent of rhodium recovery are as set forth in Table II below.

TABLE II

| Example | Salt(mmole) | Amine(mmole) | T(°C) | V Compound(mmoles) | n-propyl Alcohol, g | Methanol, g | Ethylene glycol, g | n-butyl[a] Alcohol, g | Propylene Glycol, g | Glycerine, g | % Rh Recovered |
|---|---|---|---|---|---|---|---|---|---|---|---|
| 22 | Cesium benzoate (0.65) | — | 240 | — | — | 2.15 | 2.90 | — | — | — | 27 + 52 |
| 23 | " | — | " | Triethanolamine vanadate(2.5) | 0.19 | 2.85 | 1.90 | — | 0.24 | — | 52 + 18 |
| 24 | " | — | " | Vanadium pentoxide(1.5) | 0.04 | 0.88 | 0.26 | — | — | 0.22 | 38 |
| 25 | " | — | " | Cyclopentadienyl-vanadium tetracarbonyl(3.0) | 0.10 | 2.66 | 0.05 | — | — | 0.34 | 61 |
| 26 | " | — | " | Triethyl vanadate(3.0) | 0.07 | 1.64 | — | — | — | 0.37 | 56 |
| 27 | " | — | " | Vanadyl acetate(3.0) | 0.07 | 1.37 | 0.57 | — | — | 0.27 | 68 |
| 28 | — | — | " | Cesium meta-vanadate(0.65) | 0.04 | 2.58 | 0.29 | — | — | 0.24 | 21 |

[a]Identification tentative; based on vpc retention time

In some instances certain vanadium compounds have not, under the specific reaction conditions selected, promoted the formation of n-propanol. In those instances, it is believed that the failure to produce n-propanol is a result of not selecting the appropriate reaction conditions for that particular vanadium compound. To that extent, some minor amount of experimention may be necessary to ascertain conditions under which such vanadium compounds will operate to promote n-propanol formation. For example, if the solvent is tetraglyme, a better choice may prove to be sulfolane. In some instances, merely raising the reaction temperature and/or pressure will effect the desired reaction.

What is claimed is:

1. A process for producing alkane monohydric and polyhydric alcohols in a homogeneous liquid phase mixture which comprises reacting hydrogen and oxides of carbon in the presence of a rhodium carbonyl complex and a compound of vanadium selected from the group consisting of vanadate esters, vanadium alkanedionates, alkanolamine vanadates, vanadium oxides, vanadium carbonyls, vanadyl carboxylates and salts containing vanadium oxyanions, at a temperature between about 100° C. and about 375° C. and a pressure between about 500 psia and about 50,000 psia to produce said alkane alcohols.

2. The process of claim 1 wherein the temperature is from about 220° C. to about 290° C.

3. The process of claim 1 wherein the reaction is effected in the presence of an organic solvent.

4. The process of claim 3 wherein the solvent is substituted or unsubstituted tetrahydrothiophene-1,1-dioxide.

5. The process of claim 1 wherein the reaction is effected in the presence of at least one of a Lewis base nitrogen compound or a salt.

6. The process of claim 5 wherein the salt is a carboxylate salt.

7. The process of claim 6 wherein the salt is cesium formate.

8. The process of claim 5 wherein the salt is cesium benzoate.

9. The process of claim 5 wherein the Lewis base nitrogen compound is an amine.

10. The process of claim 9 wherein the amine is pyridine.

11. The process of claim 9 wherein the amine is N-methylmorpholine.

12. The process of claim 1 wherein the alkane monohydric alcohol is n-propyl alcohol.

13. The process of claim 1 wherein the alkane polyhydric alcohol is ethylene glycol.

* * * * *

UNITED STATES PATENT AND TRADEMARK OFFICE
CERTIFICATE OF CORRECTION

PATENT NO. : 4,151,192
DATED : April 24, 1979
INVENTOR(S) : Leonard Kaplan

It is certified that error appears in the above—identified patent and that said Letters Patent are hereby corrected as shown below:

Columns 11-12, Table I, under the last column headed "% Rh Recovered", for the fifth entry reading "84+6" read -- 84+5 --.

Signed and Sealed this

First Day of January 1980

[SEAL]

Attest:

SIDNEY A. DIAMOND

Attesting Officer

Commissioner of Patents and Trademarks